United States Patent
Furuya

(10) Patent No.: US 12,285,216 B2
(45) Date of Patent: Apr. 29, 2025

(54) MEASUREMENT DEVICE

(71) Applicant: NIKON CORPORATION, Tokyo (JP)

(72) Inventor: Shunsuke Furuya, Kumagaya (JP)

(73) Assignee: NIKON CORPORATION, Tokyo (JP)

( * ) Notice: Subject to any disclaimer, the term of this patent is extended or adjusted under 35 U.S.C. 154(b) by 717 days.

(21) Appl. No.: 17/616,754

(22) PCT Filed: Jun. 10, 2019

(86) PCT No.: PCT/JP2019/022927
§ 371 (c)(1),
(2) Date: Dec. 6, 2021

(87) PCT Pub. No.: WO2020/250272
PCT Pub. Date: Dec. 17, 2020

(65) Prior Publication Data
US 2022/0330815 A1  Oct. 20, 2022

(51) Int. Cl.
*A61B 3/10* (2006.01)
(52) U.S. Cl.
CPC .................................. *A61B 3/102* (2013.01)
(58) Field of Classification Search
CPC ......... A61B 3/132; A61B 3/13; A61B 3/1225; A61B 3/1216; A61B 3/113; A61B 3/12; A61B 3/1015; A61B 3/10; A61B 3/102; G01N 21/17
USPC ....................................................... 351/206
See application file for complete search history.

(56) References Cited

U.S. PATENT DOCUMENTS

| | | | |
|---|---|---|---|
| 4,804,271 A | 2/1989 | Cammann | |
| 6,310,679 B1 * | 10/2001 | Shiraishi | G03F 7/70058 355/53 |
| 2006/0244973 A1 * | 11/2006 | Yun | G01B 9/02004 356/497 |
| 2011/0273721 A1 | 11/2011 | Kulkarni et al. | |
| 2014/0022549 A1 | 1/2014 | Ozeki | |

FOREIGN PATENT DOCUMENTS

| | | |
|---|---|---|
| JP | 2003-344650 A | 12/2003 |
| JP | 2007-085832 A | 4/2007 |
| JP | 2011-089887 A | 5/2011 |
| JP | 2011-102920 A | 5/2011 |
| WO | WO-2012/131812 A1 | 10/2012 |
| WO | WO-2015/064545 A1 | 5/2015 |

OTHER PUBLICATIONS

Office Action issued in corresponding Japanese Patent Application No. 2021-525413, dated Nov. 15, 2022.
Office Action issued in corresponding Japanese Patent Application No. 2021-525413, dated Jan. 24, 2023 (6 pages).

* cited by examiner

*Primary Examiner* — Travis S Fissel
(74) *Attorney, Agent, or Firm* — Foley & Lardner LLP

(57) ABSTRACT

A measurement device including a light source configured to emit a broad-band light beam, an interference section configured to split the broad-band light beam into a measurement light beam and a reference light beam, and to generate an interference light beam from the reference light beam and a measurement light beam reflected from an object after shining the measurement light beam onto the object, a sweeper section configured to perform wavelength sweeping of the interference light beam, and a detection section configured to detect an interference light beam output from the sweeper section.

10 Claims, 5 Drawing Sheets

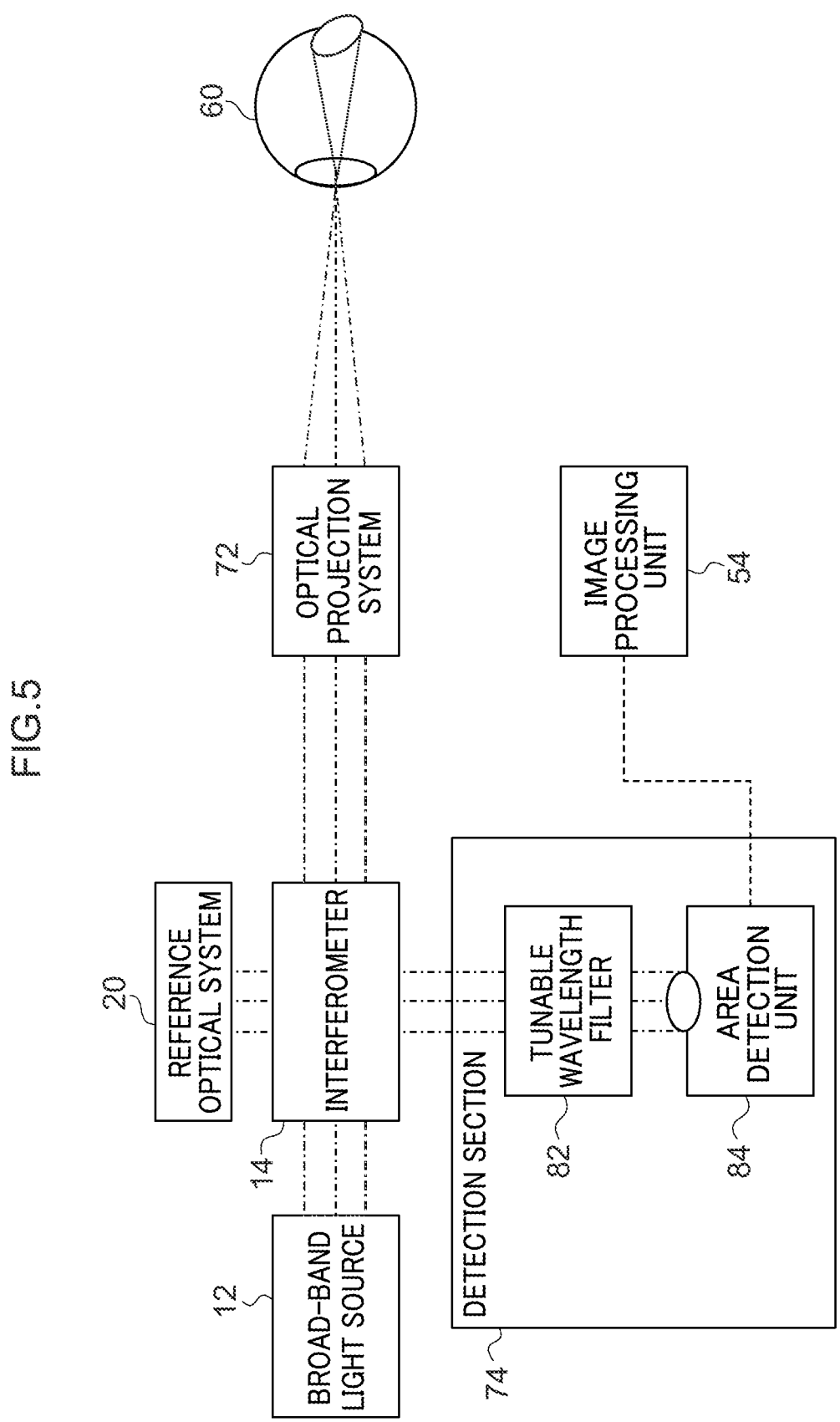

MEASUREMENT DEVICE

TECHNICAL FIELD

The present invention relates to a measurement device.

BACKGROUND ART

Optical coherence tomography devices that employ a wavelength-sweeping light source are known as imaging devices for imaging the ocular fundus or the like (Japanese Patent Application Laid-Open (JP-A) No. 2011-89887). However, such wavelength-sweeping light sources are complex in configuration.

SUMMARY OF INVENTION

A measurement device of technology disclosed herein includes a light source configured to emit a broad-band light beam, an interference section configured to split the broad-band light beam into a measurement light beam and a reference light beam, and to generate an interference light beam from the reference light beam and a measurement light beam reflected from an object, a sweeper section configured to perform wavelength sweeping of the interference light beam, and a detection section configured to detect an interference light beam output from the sweeper section.

BRIEF DESCRIPTION OF DRAWINGS

FIG. 5 is a block diagram illustrating a measurement device of a second exemplary embodiment.

DESCRIPTION OF EMBODIMENTS

Detailed explanation follows regarding exemplary embodiments of the present invention, with reference to the drawings.

First Exemplary Embodiment

Explanation follows regarding a measurement device according to a first exemplary embodiment of technology disclosed herein, with reference to the drawings. The measurement device is an optical coherence tomography (OCT) device used to acquire a tomographic image of an object.

Figure 1:
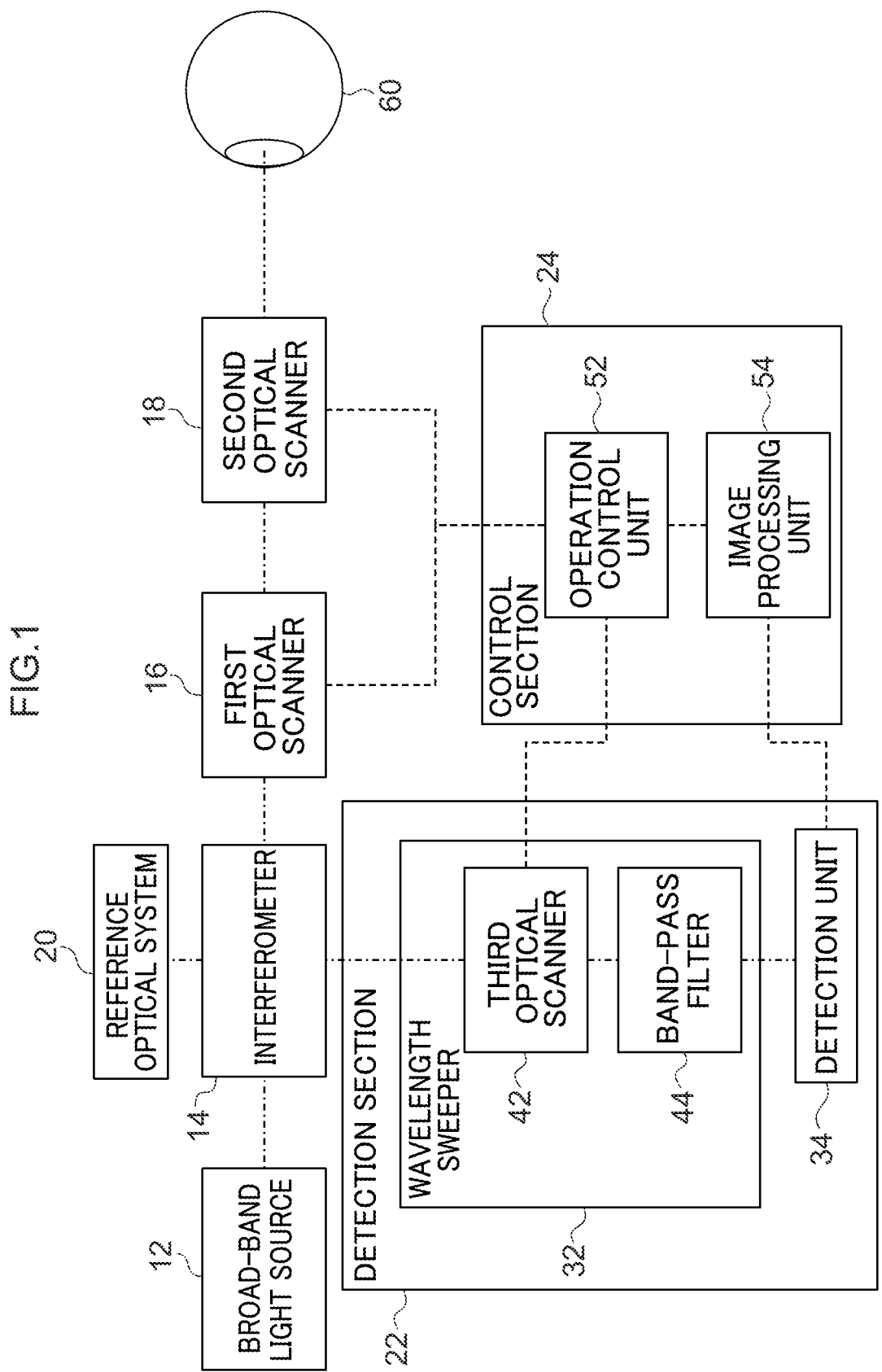
FIG. 1 is a block diagram illustrating a measurement device of a first exemplary embodiment.

FIG. 1 is a block diagram illustrating the measurement device of the first exemplary embodiment. As illustrated in FIG. 1, the measurement device includes a broad-band light source 12 that simultaneously generates plural coherent light beams having different wavelengths to each other (a broad-band light beam).

The measurement device includes an interferometer 14 and a reference optical system 20. The interferometer 14 splits light from the broad-band light source 12 into a measurement light beam and a reference light beam, and emits the measurement light beam toward an examined eye 60 while emitting the reference light beam toward the reference optical system 20.

The reference optical system 20 is configured including a movable mirror and the like. The mirror can be driven to change the length of the light path traveled by the reference light beam. The reference light beam is reflected by the mirror and returns to the interferometer 14.

The measurement device includes a first optical scanner 16 that scans the examined eye 60 in a horizontal direction with the measurement light beam, and a second optical scanner 18 that scans the examined eye 60 in a vertical direction with the measurement light beam.

The measurement light beams scanned onto the examined eye 60 by the first optical scanner 16 and the second optical scanner 18 are reflected by the fundus of the examined eye 60, and return to the interferometer 14 via the second optical scanner 18 and the first optical scanner 16.

The interferometer 14 creates an interference pattern between the reference light beam from the reference optical system 20 and the measurement light beam reflected by the fundus of the examined eye 60, and emits the result as an interference light beam.

The measurement device includes a detection section 22 and a control section 24. The detection section 22 includes a wavelength sweeper 32 configured by a third optical scanner 42 and a band-pass filter 44 and configured to sweep the interference light beam. The detection section 22 further includes a detection unit 34 configured to detect the swept interference light beam. The wavelength sweeper 32 performs a wavelength sweep of the interference light beam, configured by a broad-band light beam, so as to output a different wavelength of the interference light beam at each respective timing.

The control section 24 includes an operation control unit 52 that controls operation of the first optical scanner 16, the second optical scanner 18, and the third optical scanner 42. The control section 24 also includes an image processing unit 54 that is input with a signal from the operation control unit 52 indicating operation timings of the third optical scanner 42, and that, based on this input signal, creates a tomographic image of the examined eye 60 according to the intensity of the swept interference light beam detected by the detection unit 34.

The third optical scanner 42 of the wavelength sweeper 32 scans the interference light beam toward an incident face of the band-pass filter 44.

At the band-pass filter 44, the interference light beam from the third optical scanner 42 is scanned across the incident face of the band-pass filter 44, this being a planar face. The interference light beam is thereby shone onto the incident face at a different angle of incidence at each respective timing. The wavelengths allowed to pass through the band-pass filter 44 differ according to the angle of incidence. Namely, the band-pass filter 44 outputs a beam with a different wavelength at each respective timing in synchronization with scan timings of the third optical scanner 42.

A region of the band-pass filter 44 onto which the interference light beam is shone and through which the interference light beam passes (a region scanned by the third optical scanner 42) is configured by a multilayered film with a uniform structure. For example, the band-pass filter 44 may be configured by a multilayered dielectric film. Each film layer is configured with consistent film properties and a consistent thickness across each location within the region onto which the interference light beam is shone and through which the interference light beam passes.

Since the region of the band-pass filter 44 onto which the interference light beam is shone and through which the interference light beam passes is configured by a multilayered film with a uniform structure, the distance at which the interference light beam passes through the band-pass filter 44 varies according to the angle of incidence of the interference light beam, and the wavelength of the interference light beam allowed to pass differs accordingly.

Since the band-pass filter 44 is configured such that the wavelength of the interference light beam allowed to pass differs according to the angle of incidence, sweeping of the wavelengths of the interference light beam is synchronized with the scan cycle of the third optical scanner 42.

Note that for example, a TS laser clean-up filter (model No. #68-855) manufactured by Edmond Optics, Ltd. may be employed as the band-pass filter 44. Note that the wavelength sweeping range may be adjusted by adjusting the materials or structure (such as the thickness or composition of each layer) of the multilayered film.

A polygon mirror, a mirror galvanometer, a resonant scanner, a micro electromechanical system (MEMS) scanner, or the like may be employed as each of the first optical scanner 16, the second optical scanner 18, and the third optical scanner 42. The frequency at which the interference light beam is scanned by the third optical scanner 42 is higher than the frequency at which illuminated light beams are scanned by the first optical scanner 16 and the second optical scanner 18. For example, setting is made such that the first optical scanner 16 scans an illuminated light beam at 10 Hz, the second optical scanner 18 scans an illuminated light beam at 100 Hz, and the third optical scanner 42 scans at 50,000 Hz (50 kHz). Note that the first optical scanner and the second optical scanner may be driven at the same frequency as each other (for example 10 Hz or 100 Hz). In cases in which a mirror galvanometer or a MEMS scanner is employed as the third optical scanner 42, the third optical scanner 42 is capable of changing the scan range of the interference light beam. Specifically, the scan range can be changed by changing the amplitude of the third optical scanner 42. More specifically, changing the amplitude changes the angle range over which the interference light beam is incident to the band-pass filter 44, thereby changing the wavelength scan range changes. The wavelength scan range is enlarged as the amplitude is increased, and conversely the wavelength scan range decreases as the amplitude is reduced.

There is no particular limitation to the configuration of the wavelength sweeper 32, as long as it is a device that is able to change the extracted wavelength with time, such as a Fabry-Perot spectrometer, or an acousto-optic tunable filter (AOTF).

Figure 2A:
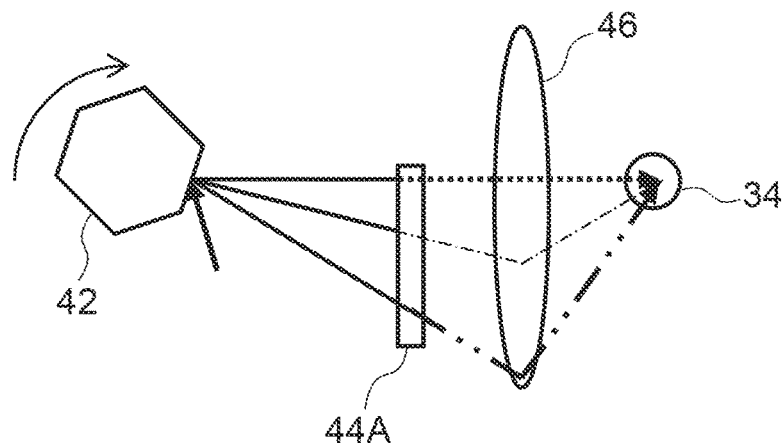
FIG. 2A is a diagram illustrating a first example of a wavelength sweeper.

Next, explanation follows regarding a first example of the wavelength sweeper 32, with reference to FIG. 2A. In the wavelength sweeper 32 of the first example illustrated in FIG. 2A, a polygon mirror is employed as the third optical scanner 42. When the interference light beam is scanned onto the incident face of a band-pass filter 44A by the third optical scanner 42, the scanned interference light beam is incident to the band-pass filter 44A at a different angle of incidence at each respective timing, such that different wavelengths of the interference light beam are emitted from the band-pass filter 44A according to the angle of incidence.

The wavelength sweeper 32 includes an optical system 46 that guides the interference light beam to a single point on a detection section of the detection unit 34 after passing through the band-pass filter 44A.

Since the interference light beam is guided by the optical system 46 to a single point on the detection section of the detection unit 34 after passing through the band-pass filter 44A, a detection unit that detects the interference light beam as a point may be employed as the detection unit 34. For example, a point detector (such as a photodiode (point sensor)) may be employed therefor.

Note that the optical system 46 may be omitted from the technology disclosed herein. In such cases, a detection unit that performs linear or planar detection of the interference light beam may be employed as the detection unit 34.

Next, explanation follows regarding operation of the measurement device of the first exemplary embodiment.

The broad-band light source 12 simultaneously generates plural coherent light beams of different wavelengths. The interferometer 14 splits the light generated by the broad-band light source 12 into an illuminated light beam and a reference light beam by the interferometer 14.

The length of the light path length traveled by the reference light beam before returning to the interferometer 14 is changed by the reference optical system 20.

Under the control of the operation control unit 52, the first optical scanner 16 and the second optical scanner 18 scan the fundus of the examined eye 60 with the illuminated light beam in the horizontal direction and the vertical direction respectively.

A reflected light beam reflected by the fundus of the examined eye 60 returns to the interferometer 14 via the second optical scanner 18 and the first optical scanner 16.

The reference light beam from the reference optical system 20 and the reflected light beam reflected by the fundus of the examined eye 60 are combined by the interferometer 14 and emitted by the wavelength sweeper 32 of the detection section 22 as an interference light beam.

Under the control of the operation control unit 52, the third optical scanner 42 (polygon mirror (see FIG. 2A)) of the wavelength sweeper 32 scans the interference light beam onto the incident face of the band-pass filter 44A.

The interference light beam is scanned onto the incident face of the band-pass filter 44A by the third optical scanner 42 such that the interference light beam shines onto the band-pass filter 44A with a different angle of incidence differs at each respective timing. A different wavelength of the interference light beam is thus emitted from the band-pass filter 44A at each respective timing.

The optical system 46 guides the different wavelengths of the interference light beam that are allowed to pass through the band-pass filter 44A at each respective timing to the detection unit 34.

As described above, the frequency at which the interference light beam is scanned by third optical scanner 42 is higher than the frequency at which the first optical scanner 16 and the second optical scanner 18 scan the examined eye 60 with the illuminated light beam in the vertical direction. This enables thickness direction information for various points on the retina at the fundus of the examined eye 60 to be acquired by scanning using the first optical scanner 16 and the second optical scanner 18.

As described above, the third optical scanner 42 of the wavelength sweeper 32 is controlled by the operation control unit 52. Observation position information acquired from the first optical scanner 16 and the second optical scanner 18 at each respective timing, as well as the signal indicating operation timings of the third optical scanner 42, are input to the image processing unit 54 from the operation control unit 52.

Thus, based on the signal indicating the operation timings of the third optical scanner 42, the image processing unit 54 is able to ascertain the rotation angle of the polygon mirror configuring the third optical scanner 42 at each respective timing, the angle of the corresponding reflective mirror of the polygon mirror at each respective timing, and the angle of incidence of the interference light beam scanned by the corresponding reflective mirror at each respective timing. The image processing unit 54 is thereby able to ascertain the wavelength of the interference light beam detected by the detection unit 34 at each respective timing, and thereby ascertain the wavelengths corresponding to the interference light beam intensities detected by the detection unit 34.

Specifically, as illustrated in FIG. 2A, the angle of incidence of the interference light beam with respect to the band-pass filter 44 changes accompanying the rotation of the polygon mirror. If employing a swept source (SS) light source, the wavelength would change at a constant rate at each respective timing. However, the rate of wavelength change in the output of the detection unit 34 does not maintain a constant rate with each respective timing. This is because the length of the light path traveled by the interference light beam from the reflective face of the polygon mirror to the detection unit via the band-pass filter 44 changes as the angle of incidence to the band-pass filter 44 changes accompanying rotation of the polygon seen. The image processing unit 54 accordingly performs signal processing using a delay filter or the like so as to obtain a constant rate of wavelength change at each respective timing from the output of the detection unit 34 that does not maintain a constant rate of wavelength change at each respective timing. A tomographic image of the examined eye 60 is then created by applying a Fourier transform to the signal following the processing to obtain a constant rate of wavelength change at each respective timing. The tomographic image includes an image illustrating a cross-section of an anterior eye portion or a posterior eye portion by a B-scan, or a 3D image of the anterior eye portion or the posterior eye portion by a C-scan.

As described above, the first exemplary embodiment obtains a measurement device that performs wavelength sweeping of an interference light beam while employing a broad-band light source that simultaneously generates light beams of different wavelengths. Providing light-splitting functionality on the detection unit side enables the use of a broad-band light source, this being lower in cost and simpler in configuration than an SS light source.

The first exemplary embodiment includes the first optical scanner 16 and the second optical scanner 18 that scan the measurement light beam in order to enable acquisition of a two-dimensional tomographic image of the fundus.

The first exemplary embodiment also includes the optical system 46 that guides the beam to the detection unit 34 after passing through the band-pass filter 44 (44A), thereby enabling a point detector (such as a photodiode) to be employed. The first exemplary embodiment thereby enables a lower cost measurement device with a simpler configuration.

The first exemplary embodiment enables a band-pass filter that has a simple, uniform (film) structure to be employed.

The broad-band light source 12, the interferometer 14, the wavelength sweeper 32, and the detection unit 34 respectively correspond to examples of a "light source", an "interference section", a "sweeper section", and a "detection section" of technology disclosed herein. The first optical scanner 16 and the second optical scanner 18 are examples of a "measurement light beam scanner section" of technology disclosed herein. The third optical scanner 42 is an example of a "sweeping scanner section" of technology disclosed herein.

Figure 2B:
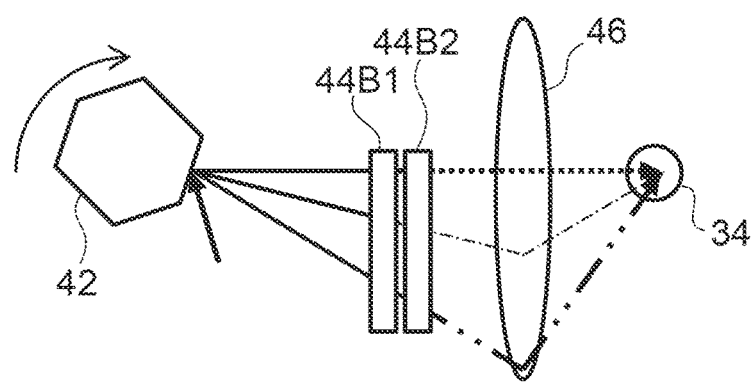
FIG. 2B is a diagram illustrating a second example of a wavelength sweeper.

Next, explanation follows regarding a second example of the wavelength sweeper 32, with reference to FIG. 2B. The second example of the wavelength sweeper 32 has substantially the same configuration as the first example of the wavelength sweeper 32 illustrated in FIG. 2A, and so the same reference numerals are allocated to equivalent portions and explanation thereof is omitted. Explanation follows regarding only portions that differ to those in the first example. As illustrated in FIG. 2B, instead of the band-pass filter 44A, the wavelength sweeper 32 includes a long-pass filter 44B1 disposed on the third optical scanner 42 side, and a short-pass filter 44B2 disposed on the detection unit 34 side. Note that alternatively, the short-pass filter 44B2 may be disposed on the third optical scanner 42 side and the long-pass filter 44B1 disposed on the detection unit 34 side.

The long-pass filter 44B1 and the short-pass filter 44B2 are each configured by a multilayered film with a uniform structure at a region onto which the interference light beam is shone and through which the interference light beam passes. The wavelength of the interference light beam allowed to pass through differs according to the angle of incidence.

The overall long-pass filter 44B1 allows the passage of the interference light beam within a first wavelength range, and the overall short-pass filter 44B2 allows the passage of the interference light beam within a second wavelength range, the second wavelength range being further toward the short wavelength side than the first wavelength range. Overall, the long-pass filter 44B1 and the short-pass filter 44B2 allow the passage of wavelengths of the interference light beam within a range corresponding to a predetermined range of wavelengths of the interference light beam that are allowed to pass by the band-pass filter 44A illustrated in FIG. 2A. Namely, a range obtained by overlaying the first range and the second range corresponds to this predetermined range.

As illustrated from the top to the bottom of the page in FIG. 2B, for each position scanned with the interference light beam by the third optical scanner 42, interference light of λk or longer (where k=1, 2, 3, . . . n) passes through the long-pass filter 44B1. Next, at the short-pass filter 44B2, as illustrated from the top to the bottom of the page in FIG. 2B, for each position where the interference light beam has passed through the long-pass filter 44B1, interference light of λk or shorter passes through the short-pass filter 44B2. As a result, only light of λk in the light beam passes through the long-pass filter 44B1 at the respective positions from the top to the bottom of the page in FIG. 2B. Note that the entire range of wavelengths λk corresponds to the predetermined range described previously.

Figure 2C:
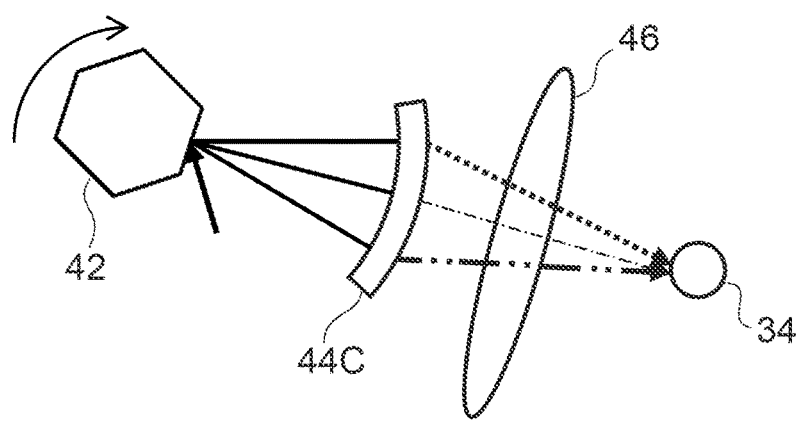
FIG. 2C is a diagram illustrating a third example of a wavelength sweeper.

Next, explanation follows regarding a third example of the wavelength sweeper 32, with reference to FIG. 2C. The third example of the wavelength sweeper 32 has substantially the same configuration as the first example of the wavelength sweeper 32 illustrated in FIG. 2A, and so the same reference numerals are allocated to equivalent portions and explanation thereof is omitted. Explanation follows regarding only portions that differ to those in the first example. As illustrated in FIG. 2C, instead of the band-pass filter 44A, the wavelength sweeper 32 includes a band-pass filter 44C. The band-pass filter 44C is configured such that each position through which light is capable of passing allows light of a different wavelength to pass through, even for the same angle of incidence. The overall band-pass filter 44C allows the passage of wavelengths of the interference light beam within the predetermined range described previously.

Figure 3A:
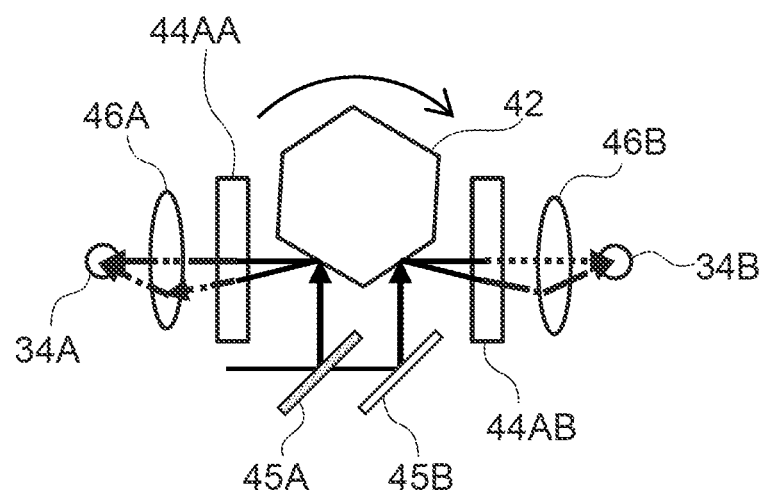
FIG. 3A is a diagram illustrating a fourth example of a wavelength sweeper.

Next, explanation follows regarding a fourth example of the wavelength sweeper 32, with reference to FIG. 3A. The wavelength sweeper 32 of the fourth example includes a beam splitter 45A and a mirror 45B. The beam splitter 45A splits the interference light beam into two, with one of the resulting interference light beams being reflected by the third optical scanner 42 and the other of the resulting interference light beams passing through the beam splitter 45A. The mirror 45B reflects the other interference light beam that has passed through the beam splitter 45A toward the third optical scanner 42.

In the wavelength sweeper 32 of the fourth example, the beam splitter 45A and the mirror 45B cause interference light beams to be incident to two separate faces of the third optical scanner 42.

The wavelength sweeper 32 includes a band-pass filter 44AA at a position where the one interference light beam reflected by the beam splitter 45A is scanned by the third optical scanner 42, and a band-pass filter 44AB at a position where the other interference light beam reflected by the mirror 45B is scanned by the third optical scanner 42.

The wavelength sweeper 32 also includes a detection unit 34A that detects the interference light beam that has passed through the band-pass filter 44AA, and a detection unit 34B that detects the interference light beam that has passed through the band-pass filter 44AB.

The wavelength sweeper 32 also includes an optical system 46A that guides the interference light beam that has passed through the band-pass filter 44AA onto the detection unit 34A, and an optical system 46B that guides the interference light beam that has passed through the band-pass filter 44AB onto the detection unit 34B.

The band-pass filter 44AA and the band-pass filter 44AB are both configured to allow the passage of different wavelengths of the interference light beam according to the angle of incidence, and are also configured so as to allow the passage of different wavelength ranges of the interference light beams overall. For example, overall, the wavelength range of the interference light beam that is allowed to pass through the band-pass filter 44AA is a range spanning from the center of the predetermined range described previously toward the short wavelength side, whereas overall, the wavelength range of the interference light beam that is allowed to pass through the band-pass filter 44AB is a range spanning from the center of the predetermined range described previously toward the long wavelength side.

In this manner, the third optical scanner 42 causes interference light beams to be incident to the band-pass filter 44AA and the band-pass filter 44AB that allow the passage of mutually different wavelength ranges of the interference light beam while the angle of the respective interference light beams changes with time, such that only wavelengths of the interference light beams corresponding to the angle of incidence pass through. The passage of these interference light beams is detected by the separate detection units 34A, 34B, enabling intensity information to be obtained for each wavelength. The fourth configuration enables the swept wavelength range to be enlarged while reducing the time required to perform a wavelength sweep.

Note that in the fourth example, in addition to splitting the interference light beam into two, the respective interference light beams are made incident to two band-pass filters, namely the band-pass filter 44AA and the band-pass filter 44AB, each allowing the passage of a different wavelength range of the respective interference light beam. However, the technology disclosed herein is not limited thereto, and the interference light beam may be split into three or more, with the resulting interference light beams being made incident to three or more respective band-pass filters, each allowing the passage of a different wavelength range of the respective interference light beam.

Figure 3B:
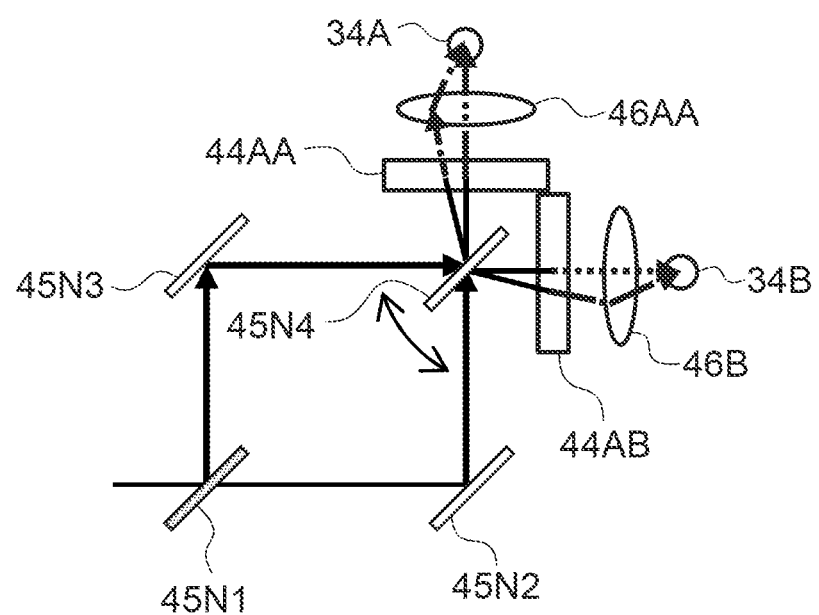
FIG. 3B is a diagram illustrating a fifth example of a wavelength sweeper.

Next, explanation follows regarding a fifth example of the wavelength sweeper 32, with reference to FIG. 3B. The wavelength sweeper 32 of the fifth example has similar configuration elements to the fourth example, and so the same reference numerals are allocated to equivalent portions and explanation thereof is omitted. Explanation follows regarding only portions that differ to those in the fourth example.

The wavelength sweeper 32 includes a beam splitter 45N1, a mirror 45N3, a mirror 45N2, and a mirror 45N4. The beam splitter 45N1 splits the interference light beam into two, reflecting one of the resulting interference light beams and allowing the other resulting interference light beam to pass through. The mirror 45N3 reflects the reflected one interference light beam, the mirror 45N2 reflects the other interference light beam that has passed through, and the mirror 45N4 is disposed so as to be capable of pivoting. The mirror 45N3 reflects the one interference light beam toward a reflective face of the mirror 45N4, and the mirror 45N2 reflects the other interference light beam toward another reflective face of the mirror 45N4. The mirror 45N4 pivots such that the one interference light beam is scanned by the one reflective face, and the other interference light beam is scanned by the other reflective face. The band-pass filter 44AA is disposed on the side where the one interference light beam is scanned, and the band-pass filter 44AB is disposed on the side where the other interference light beam is scanned. After passing through the band-pass filter 44AA, the one interference light beam is guided to the detection unit 34A by an optical system 46AA, and detected by the detection unit 34A. After passing through the band-pass filter 44AB, the other interference light beam is guided to the detection unit 34B by an optical system 46B, and detected by the detection unit 34B.

The fifth example also enables the swept wavelength range to be enlarged while reducing the time required to perform a wavelength sweep.

Note that in the fifth example, the mirror 45N3 and the mirror 45N2 may be replaced by beam splitters so as to split the respective interference light beams further, with interference light beams that have passed through the respective beam splitters being scanned onto separate band-pass filters by pivoting mirrors. After passing through the separate band-pass filters, the interference light beams may then be guided to separate detection units by corresponding optical systems and detected by these detection units.

Figure 4A:
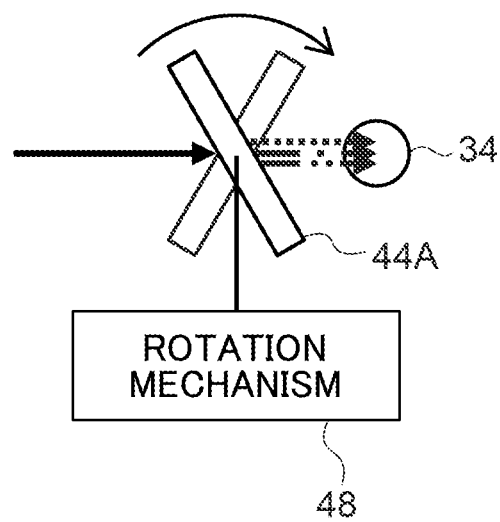
FIG. 4A is a diagram illustrating a sixth example of a wavelength sweeper.

Next, explanation follows regarding a sixth example of the wavelength sweeper 32, with reference to FIG. 4A. The wavelength sweeper 32 of the sixth example has similar configuration elements to the first example, and so the same reference numerals are allocated to equivalent portions and explanation thereof is omitted. Explanation follows regarding only portions that differ to those in the first example. As illustrated in FIG. 4A, the band-pass filter 44A of the wavelength sweeper 32 is disposed so as to be capable of pivoting, such that the angle of incidence of interference light beams changes with time. The wavelength sweeper 32 includes a rotation mechanism 48 that rotates the band-pass filter 44A such that the angle of incidence of the interference light beam changes with time. The detection unit 34 is disposed beyond the band-pass filter 44A.

Figure 4B:
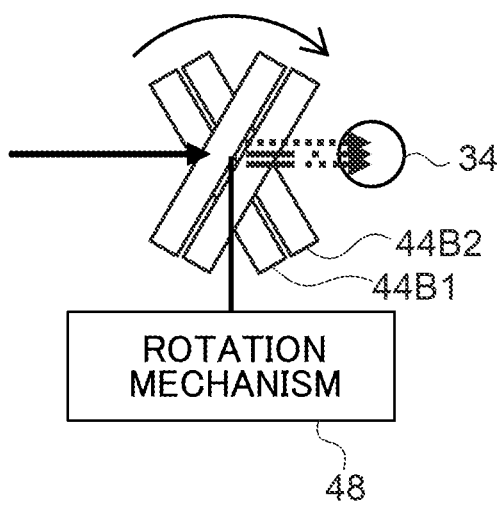
FIG. 4B is a diagram illustrating a seventh example of a wavelength sweeper.

Next, explanation follows regarding a seventh example of the wavelength sweeper 32, with reference to FIG. 4B. The wavelength sweeper 32 of the seventh example has similar configuration elements to the first example and the sixth example, and so explanation follows regarding only portions that differ thereto. As illustrated in FIG. 4B, in the seventh example, instead of the band-pass filter 44A of the sixth example, the long-pass filter 44B1 and the short-pass filter 44B2 are rotated by the rotation mechanism 48 such that angle of incidence of the interference light beam changes with time.

In the sixth and seventh examples of the wavelength sweeper 32, the interference light beam is not scanned, and so the interference light beam arrives at a single point on the detection section of the detection unit 34 after passing through the band-pass filter 44A, or the long-pass filter 44B1 and the short-pass filter 44B2, without the need to employ an optical system 46. Thus, sixth and seventh examples of the wavelength sweeper 32 enable a point detector (such as a photodiode) to be used as the detection unit 34 without the need to employ an optical system 46.

The second example (FIG. 2B) and the seventh example (FIG. 4B) of the wavelength sweeper 32 include the long-pass filter 44B1 and the short-pass filter 44B2. However, the technology disclosed herein is not limited thereto. For example, instead of the long-pass filter 44B1 and the short-pass filter 44B2, a configuration may be applied in which a single (glass) substrate has a first face and a second face opposing the first face, with a long-pass filter film being formed on one face out of the first face or the second face, and a short-pass filter film being formed on the other face out of the first face or the second face.

Second Exemplary Embodiment

Next, explanation follows regarding a second exemplary embodiment of technology disclosed herein. The second exemplary embodiment has similar configuration elements to the first exemplary embodiment, and so the same reference numerals are allocated to equivalent portions and explanation thereof is omitted. Explanation follows regarding only portions that differ to those in the first exemplary embodiment.

FIG. 5 is a block diagram illustrating a measurement device of the second exemplary embodiment. As illustrated in FIG. 5, the measurement device of the second exemplary embodiment is applied to OCT (full field OCT) in which a predetermined region (rather than a single point) of the fundus of the examined eye 60 is imaged in a single take.

The broad-band light source 12 of the measurement device of the second exemplary embodiment generates a luminous flux including coherent light beams of plural wavelengths. Note that an LED may be employed as the broad-band light source 12. The interferometer 14 splits the light of a predetermined light beam formation into a measurement light beam formation and a reference light beam formation. A beam splitter or the like may be employed as the interferometer 14.

Instead of the first optical scanner 16 and the second optical scanner 18, the measurement device includes an optical projection system 72 that guides the measurement light beam formation toward a measurement region of the fundus of the examined eye 60. Thus, in the second exemplary embodiment, the measurement region of the object to be measured is illuminated by the measurement light beam formation in a single take. A position illuminated by the measurement light beam formation is moved by a non-illustrated scanner or the like included in the optical projection system, thereby enabling the measurement region to be moved.

A detection section 74 of the measurement device includes a tunable wavelength filter 82 that performs a wavelength sweep of the interference light beams at each respective timing, and an area detection unit 84. The tunable wavelength filter 82 may be configured by any device that is able to change the extracted wavelength with time, such as a Fabry-Perot resonator, or an acousto-optic tunable filter (AOTF). The area detection unit 84 is disposed so as to be conjugate to the retina at the fundus of the examined eye 60.

The interferometer 14 merges the measurement light beam formation reflected back from the fundus of the examined eye 60 with the reference light beam formation, and emits the result toward the tunable wavelength filter 82 of the detection section 74 as the interference light beam formation.

The tunable wavelength filter 82 performs a wavelength sweep of the interference light beam formation at each respective timing. The interference light beam formation that has passed through the tunable wavelength filter 82 is detected by the area detection unit 84.

The wavelengths swept by the tunable wavelength filter 82 at each respective timing are set in advance. Thus, interference light beam intensity information is output from the area detection unit 84 to the image processing unit 54 in a predetermined wavelength sequence. The image processing unit 54 applies a Fourier transform to the respective wavelength intensity information to create a tomographic image of the measurement region of the fundus of the examined eye 60.

Performing a spectral wavelength sweep in the above manner enables a full field OCT to be realized with a simple configuration.

The second exemplary embodiment proposes technology as follows.

A measurement device including:

a light source configured to emit a broad-band light beam;

an interference section configured to split the light beam emitted by the light source into a measurement light beam and a reference light beam, and to generate an interference light beam from the reference light beam and a measurement light beam reflected from an object after shining the measurement light beam onto the object in a single take;

a sweeper section configured to sweep the interference light beam so as to give a different light wavelength at each respective timing; and a detection section configured to detect the interference light beam swept so as to give a different light wavelength at each of the respective timings, wherein the sweeper section includes a tunable wavelength filter configured to sweep an interference light beam of a predetermined light beam formation so as to give a different light wavelength at each respective timing.

Although the first exemplary embodiment and the second exemplary embodiment described are directed toward the acquisition of a tomographic image of the fundus (posterior eye portion) of the examined eye 60, the technology disclosed herein is not limited thereto. For example, the technology disclosed herein may be applied to acquire a tomographic image of the anterior eye portion of the examined eye 60. Furthermore, the subject of the acquired tomographic image may be the teeth, or an internal site within a living body such as the esophagus, bronchial tube, or large intestine. Furthermore, the technology disclosed herein may be applied to capture of a tomographic image of minerals or components instead of part of a living body. The technology disclosed herein enables image acquisition to be performed with high sensitivity at a similar speed to wavelength sweeping OCT (SS-OCT) using a broad-band light source with a simple configuration.

EXPLANATION OF THE REFERENCE NUMERALS 12 broad-band light source
14 interferometer
16 first optical scanner
18 second optical scanner
20 reference optical system
22 detection section
24 control section
32 wavelength sweeper
34, 34A, 34B detection unit
42 third optical scanner
44, 44A, 44AA, 44AB, 44C band-pass filter
44B1 long-pass filter
44B2 short-pass filter
45A beam splitter
45B mirror
45N1 beam splitter
45N2, 45N3, 45N4 mirror
46, 46A, 46B optical system
48 rotation mechanism
52 operation control unit
54 image processing unit
60 examined eye
72 optical projection system
74 detection section
82 tunable wavelength filter
84 area detection unit

The invention claimed is:

1. A measurement device comprising:
    a light source configured to emit light beams of different wavelengths;
    an interference section configured to split the light beams of different wavelengths into a measurement light beam and a reference light beam, and to generate an interference light beam from the reference light beam and a reflected measurement light beam reflected from an object after shining the measurement light beam onto the object;
    a scanner section configured to scan the interference light beam from a first incidence position to a second incidence position on a scanning face;
    a band-pass filter having the scanning face, the band-pass filter allowing passage of light beams of different wavelengths based on an incident position of the interference light beam scanned by the scanner section at a constant angle of incidence; and
    a detection unit that detects the interference light beams of different wavelengths that have passed through the band-pass filter.

2. The measurement device of claim 1, wherein the band-pass filter is configured with a curved shape that is scanned so that the angle of incidence of the interference light beam is constant.

3. The measurement device of claim 1, wherein the band-pass filter is configured such that a distance from an emission point of the interference light in the scanner section to an incidence point of the interference light in the band-pass filter is constant from the first incidence position to the second incidence position of the interference light beam in the band-pass filter.

4. The measurement device of claim 1, wherein:
    the scanner section includes a reflective face; and
    the incidence position of the interference light beam with respect to the band-pass filter is changed by changing an angle of the reflective face so as to scan the interference light beam across the band-pass filter.

5. The measurement device of claim 1, wherein the scanner section is a polygon mirror.

6. The measurement device of claim 1, further comprising a light-converging optical system disposed between the band-pass filter and the detection unit, the light-converging optical system being configured to cause the interference light beam that has passed through the band-pass filter to converge on the detection unit.

7. The measurement device of claim 1, further comprising a measurement light beam scanner section configured to scan the measurement light beam across the object, wherein:
    the scanner section is driven at a first frequency, and the measurement light beam scanner section is driven at a second frequency lower than the first frequency.

8. The measurement device of claim 1, wherein the detection unit is a point sensor configured to pick up light within a wavelength sweep range swept by the band-pass filter.

9. The measurement device of claim 1, further comprising an image creation section configured to create a tomographic image of the object based on a detection signal from the detection unit.

10. The measurement device of claim 1, wherein the object is an anterior eye portion or a posterior eye portion of an examined eye.

* * * * *